(12) United States Patent
Govari et al.

(10) Patent No.: US 12,329,578 B2
(45) Date of Patent: Jun. 17, 2025

(54) VISUALIZING A MEDICAL PROBE IN A FOUR-DIMENSIONAL ULTRASOUND IMAGE

(71) Applicant: BIOSENSE WEBSTER (ISRAEL) LTD., Yokneam (IL)

(72) Inventors: Assaf Govari, Haifa (IL); Andres Claudio Altmann, Haifa (IL); Roy Urman, Irvine, CA (US); Morris Ziv-Ari, Atlit (IL); Lior Zar, Poria Illit (IL); Brandon Andrew Tran, Madison, WI (US); Shaked Meitav, Atlit (IL); Hanna Cohen-Sacomsky, Zichron Ya'acov (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 177 days.

(21) Appl. No.: 17/975,283

(22) Filed: Oct. 27, 2022

(65) Prior Publication Data

US 2023/0190235 A1 Jun. 22, 2023

Related U.S. Application Data

(60) Provisional application No. 63/291,588, filed on Dec. 20, 2021.

(51) Int. Cl.
*A61B 8/00* (2006.01)
(52) U.S. Cl.
CPC ............ *A61B 8/463* (2013.01); *A61B 8/4254* (2013.01); *A61B 8/483* (2013.01)

(58) Field of Classification Search
CPC ............ A61B 34/20; A61B 2034/2051; A61B 8/4254; A61B 2034/2063; A61B 8/483; A61B 8/463; A61B 2017/3413
See application file for complete search history.

(56) References Cited

U.S. PATENT DOCUMENTS

| | | | |
|---|---|---|---|
| 8,364,242 B2 | 1/2013 | Li | |
| 11,039,883 B1 | 6/2021 | Boveja et al. | |
| 2008/0287783 A1 | 11/2008 | Anderson | |
| 2013/0231557 A1 | 9/2013 | Li et al. | |
| 2014/0187919 A1 | 7/2014 | Parthasarathy et al. | |
| 2016/0143615 A1 | 5/2016 | Tahmasebi et al. | |
| 2016/0228095 A1 | 8/2016 | Salal et al. | |
| 2019/0380679 A1* | 12/2019 | Bharat ................ | A61B 8/5253 |
| 2020/0179057 A1* | 6/2020 | Turgeman ............. | A61B 34/20 |
| 2020/0214768 A1 | 7/2020 | Baumann et al. | |

(Continued)

OTHER PUBLICATIONS

International Search Report mailed Feb. 6, 2023 from corresponding PCT application PCT/IB2022/060769.

*Primary Examiner* — Gerald Johnson
(74) *Attorney, Agent, or Firm* — Smith, Gambrell & Russell, LLP; Michael J. Riesen

(57) ABSTRACT

Medical systems and methods are provided in which a processor receives the 3D ultrasound images and receives position signals from a position tracking device, indicating the position of a corresponding probe relative to the 3D ultrasound images. Based on the probe position, a region of interest is selected that contains the position the medical probe within the 3D ultrasound images, and the selected region of interest is rendered to a display together with a representation of the medical probe superimposed on the region of interest.

23 Claims, 8 Drawing Sheets

(56) References Cited

U.S. PATENT DOCUMENTS

| | | | |
|---|---|---|---|
| 2020/0281661 A1* | 9/2020 | Govari | A61B 5/066 |
| 2020/0390417 A1* | 12/2020 | Gijsbers | A61B 8/0883 |
| 2021/0085287 A1* | 3/2021 | Hennersperger | A61B 8/5207 |
| 2021/0275146 A1* | 9/2021 | Schlenger | A61B 8/4263 |
| 2022/0104794 A1* | 4/2022 | De Beni | G06N 20/00 |
| 2022/0241024 A1* | 8/2022 | Poland | A61B 8/0841 |

* cited by examiner

VISUALIZING A MEDICAL PROBE IN A FOUR-DIMENSIONAL ULTRASOUND IMAGE

CROSS REFERENCE TO RELATED APPLICATION

The present application claims the benefit of U.S. Provisional Application 63/291,588 of Govari et al., filed Dec. 20, 2021.

FIELD OF THE INVENTION

The present invention relates generally to medical systems, and particularly to intra-body medical probes and ultrasound imaging.

BACKGROUND

Three-dimensional (3D) ultrasound is a medical ultrasound technique often used in, for example, fetal, cardiac, trans-rectal and intra-vascular applications. 3D ultrasound refers specifically to the volume rendering of ultrasound data. When involving a series of 3D volumes collected over time, it is commonly referred to as 4D ultrasound (three spatial dimensions plus one temporal dimension).

Ultrasound imaging may be used to image a bodily tissue while a medical probe, inserted in the tissue, is used for performing a diagnostic or therapeutic procedure on the tissue.

The present invention will be more fully understood from the following detailed description of the examples thereof, taken together with the drawings in which:

DETAILED DESCRIPTION

Figure 1:
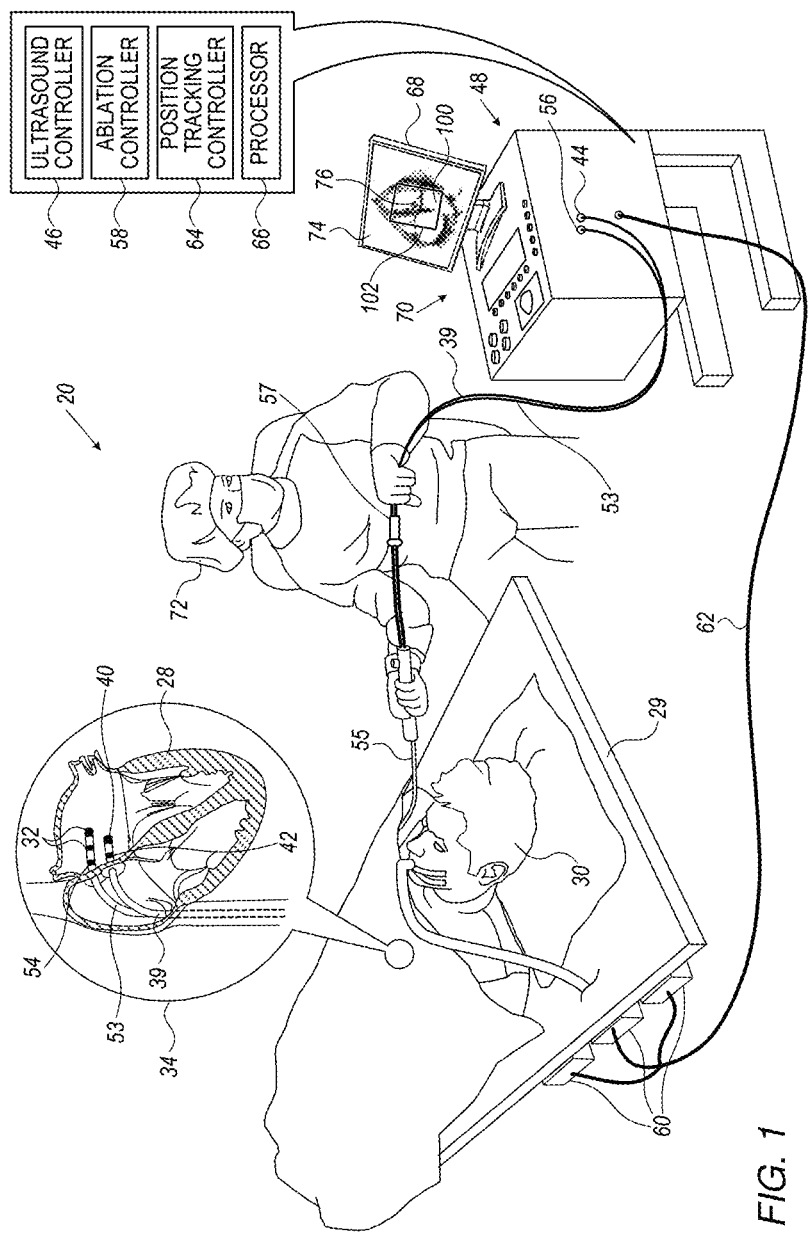
FIG. 1 is a schematic pictorial illustration of a medical system, in accordance with an aspect of the invention.

Medical probes comprising transducers are used to perform medical procedures, such as diagnostic and/or therapeutic procedures, on tissues inside the body of a living subject. A physician performing such a medical procedure may utilize one or more medical imaging modalities in order to see where the medical probe is positioned within the body of the patient. One such imaging modality is 4D ultrasound imaging, which generates 3D volumes of ultrasound data, commonly referred to as 3D ultrasound images, of selected tissue within the patient's body over consecutive instances in time. However, it is often difficult for the physician to clearly see the medical probe and to track its changing position in real time within the 3D ultrasound images. Moreover, when multiple probes are used, the physician may not be able to identify each one of them rapidly and with a high level of confidence.

To address this problem in aspects of the present invention, the medical probe comprises, in addition to the transducer, a tracking device, which enables real-time 3D tracking of the position of the medical probe relative to the ultrasound probe and thus relative to the 3D ultrasound image. This known position of the medical probe enables the imaging system to select a region of interest of the image containing the medical probe. The selected region of interest is rendered to a display screen, with the position of the medical probe superimposed on the region of interest as an icon with a distinct shape and/or color.

The region of interest may be selected either as a two-dimensional (2D) slice or a 3D sub-volume of the original 3D image. A 2D image slice may be defined as a slice that contains the longitudinal axis of the medical probe and/or a slice that is perpendicular to a surface of the tissue that the transducer of the medical probe is touching. When a change is detected in the position of the medical probe relative to the ultrasound image, the selected region of interest is updated automatically based on the detected change, without requiring intervention by the user. Once an initial region of interest has been selected, any image updates due to changes of the position of the medical probe can be limited to that region of interest. The full field of view of the 3D ultrasound image does not need to be updated, thus increasing the available frame rate for the selected region of interest and enabling real-time observation of the position of the medical probe.

In the disclosed examples, the transducer of the medical probe comprises one or more electrodes, which are used for diagnostic and/or therapeutic purposes. Alternatively, the transducer could be of a different type for application of energy to or receiving energy from the tissue, such as a thermal or acoustic transducer.

When multiple medical probes, each comprising a respective position tracking device, are simultaneously inserted in a patient's body, multiple regions of interest can be defined, each containing the respective position of one (or more) of the probes. In order to assist the physician in identifying the individual probes, each probe can be represented within its respective region of interest, as rendered to the display screen, by an icon that has a unique shape and/or color for that probe. When separate 2D slices are selected as the respective regions of interest for the probes, the 2D slices may be rendered to the display screen either simultaneously or consecutively.

Thus, in the disclosed examples, a medical system comprises a display screen, an ultrasound imaging probe, at least one medical probe, and a processor. The ultrasound imaging probe is inserted into a body of a living subject and generates 3D ultrasound images of tissue in the body. Each medical probe comprises a respective position tracking device and a transducer configured to contact the tissue. The processor receives the 3D ultrasound images and receives position signals from each position tracking device, indicating the position of the corresponding probe relative to the 3D ultrasound images. Based on the probe position, the processor selects a region of interest that contains the position of each of the medical probes within the 3D ultrasound images, and renders the selected region of interest to the display screen together with a representation of the medical probe superimposed on the regions of interest.

FIG. 1 is a schematic pictorial illustration of a medical system 20, in accordance with an aspect of the invention.

Medical system 20 comprises a 3D ultrasound imaging sub-system, an ablation sub-system, and a position tracking sub-system.

By way of example, medical system 20 is used in the present description in a radio-frequency (RF) ablation procedure of a heart 28 of a patient 30 lying on a surgical table 29. This procedure uses a medical probe in the form of an ablation catheter 53. (The distal end of catheter 53 within heart 28 is shown in an enlarged inset 34.) Alternatively or additionally, the principles of the present invention may be applied to monitoring one or more medical probes of other types inside the heart or other organs of a patient.

The ultrasound imaging sub-system comprises an ultrasound catheter 39, having a distal end comprising a 2D ultrasound transducer array 40 and a position tracking device 42, which is pre-registered with the 2D ultrasound array. A proximal end 44 of catheter 39 is connected to an ultrasound controller 46 and to a position tracking controller 64 (detailed hereinbelow), both located in a control console 48. Ultrasound controller 46 comprises electronic driver and interface circuits for driving 2D ultrasound transducer array 40 (e.g., in a phased array manner that includes steering an ultrasound beam), for receiving echo signals from the array, and for communicating with a processor 66 located in console 48.

The ablation sub-system comprises ablation catheter 53, along with an ablation controller 58. Catheter 53 comprises a position tracking device 54 and multiple electrical transducers in the form of electrodes 32, which are arranged along the distal end of the catheter and contact tissue within heart 28. Electrodes 32 are pre-registered with position tracking device 54. A proximal end 56 of catheter 53 is connected to ablation controller 58 and to position tracking controller 64 within control console 48. Ablation controller 58 comprises electronic driver and interface circuits for driving, under the control of processor 66, ablation currents through electrodes 32, as well as for communicating with processor 66. Additionally or alternatively, console 48 may comprise sensing circuits for receiving and processing electrical signals received by electrodes 32 from the heart tissue.

The position tracking sub-system comprises magnetic field generators 60, which are attached to surgical table 29 and are connected by a cable 62 to position tracking controller 64. Position tracking controller 64 comprises electronic driver and interface circuits for driving currents to generators 60, as well as for communicating with processor 66. The currents sent by position tracking controller 64 to generators 60 generate magnetic fields, which induce position signals in the respective position tracking devices 42 and 54. These position signals are coupled to position tracking controller 64 through catheters 39 and 53, respectively. Controller 64 processes the position signals in order to compute location and orientation coordinates of tracking devices 42 and 54 for input to processor 66. This sort of magnetic position tracking sub-system is used, for example, in the CARTO® system sold by Biosense Webster Inc. (Irvine, California). Alternatively or additionally, system 20 may comprise other sorts of position tracking sub-systems that are known in the art, such as sub-systems based on sensing of electrical impedance.

Control console 48 comprises, in addition to controllers 46, 58, 64, and processor 66, a display screen 68 and user input devices 70 (such as, for example, a keyboard and a trackball mouse).

Processor 66 typically comprises a general-purpose computer, with suitable interface circuits for communicating with controllers 46, 58, and 64, as well as with display screen 68 and input devices 70. Processor 66 is typically programmed in software to carry out the functions described herein. The software may be downloaded to the processor in electronic form, over a network, for example, or it may, alternatively or additionally, be provided and/or stored on non-transitory tangible media, such as magnetic, optical, or electronic memory. Processor 66 may also include memory for storing data and programs.

In preparation for the ablation procedure, a physician 72 inserts catheters 39 and 53 through a sheath 55 (or alternatively through two separate sheaths) into heart 28 of patient 30. Physician 72 navigates the distal ends of the catheters to target positions in heart 28 using a manipulator 57 near the proximal ends of the two catheters.

Prior to and during the ablation procedure, processor 66 receives 3D ultrasound images from ultrasound controller 46 and receives position coordinates from position tracking controller 64 indicating the position of catheter 53 relative to the 3D ultrasound images. Based on the indicated position, processor 66 selects a region of interest 100 that contains the distal end of catheter 53 within the 3D ultrasound images, and renders an image 74 of the selected region of interest to display screen 68. Processor 66 further displays an icon 76, as a representation of the distal end of catheter 53, on image 74, based on the relative 3D positions provided by position tracking controller 64. Icon 76 is shown as a distinct shape and/or with a distinct color so that it is easily recognizable against image 74.

Region of interest 100 may be a 2D slice or a 3D sub-volume of the 3D ultrasound image. In either case, after region of interest 100 has been selected, only this region needs to be imaged by the 3D ultrasound imaging sub-system, thus increasing the available frame rate and enabling real-time observation of the position of the distal end of ablation catheter 53 during the procedure. The 2D slice may be taken along a plane that contains the longitudinal axis of the distal end of ablation catheter 53 or along a plane that is perpendicular to the surface of the tissue of heart 28 with which the distal end is in contact. When ablation catheter 53 is deflected, the 2D slice may be selected to coincide with the plane of deflection. However, the orientation of the slice is not limited to the position and orientation of ablation catheter 53, but may alternatively be selected based on the position and orientation of other catheters or based on positions and orientations of anatomical markers.

Processor 66 may select region of interest 100 autonomously. Alternatively, physician 72 may select an initial region of interest within a 3D ultrasound image, for example by using input devices 70 to mark a frame 102 containing icon 76 within the 3D ultrasound image. To choose a 2D slice as region of interest 100, physician 72 may manipulate the full 3D ultrasound image by rotating it, for example using input devices 70, and/or by viewing on display screen 68 selected 2D slices at various orientations and spatial positions. For selecting a 3D sub-volume as a region of interest, physician 72 will, similarly to selecting a 2D slice, manipulate the full 3D image by using input devices 70 and by viewing the manipulated images on display screen 68. After the physician has selected the initial region of interest, processor 66 will automatically update the location and orientation of the region of interest shown in image 75 as needed, for example based on the location and orientation of the distal end of catheter 53.

Figure 2A:
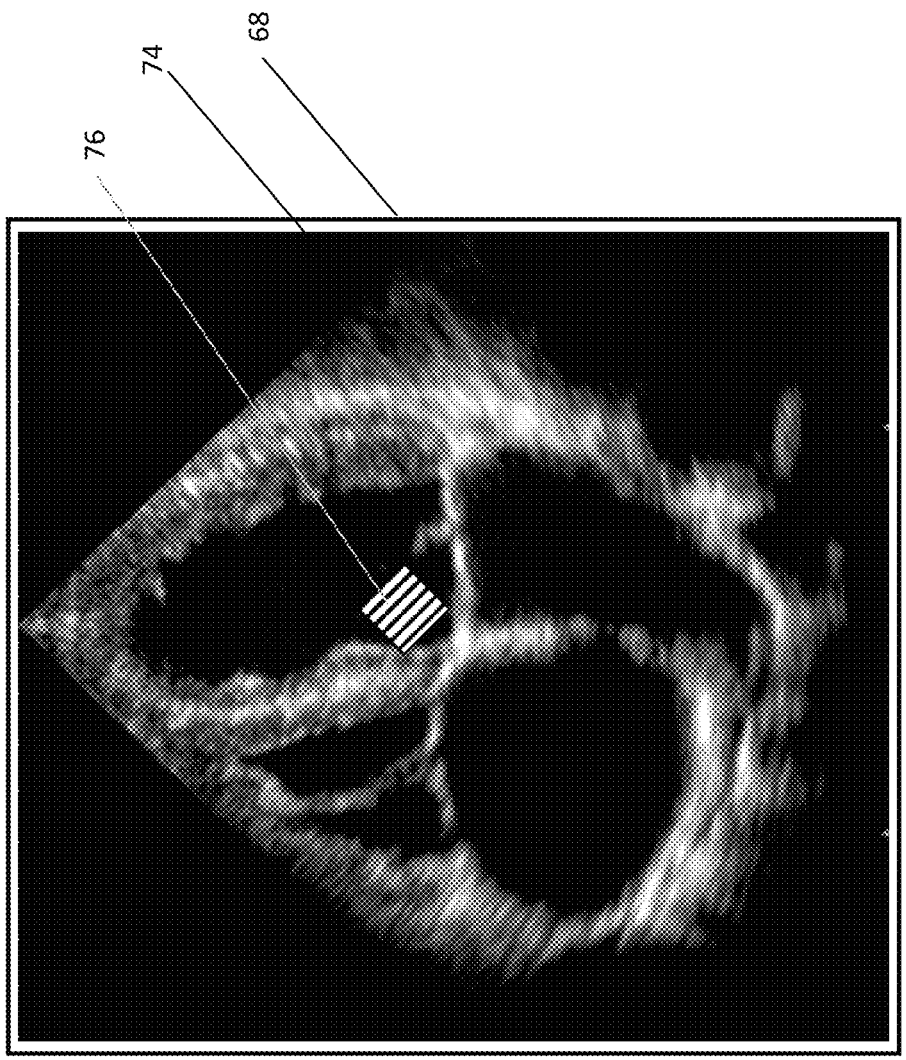
FIGS. 2A, 2B, and 2C are schematic representations of ultrasound images of a heart, illustrating a process of selection of a region of interest for visualizing a medical probe, in accordance with an aspect of the invention.
Figure 2B:
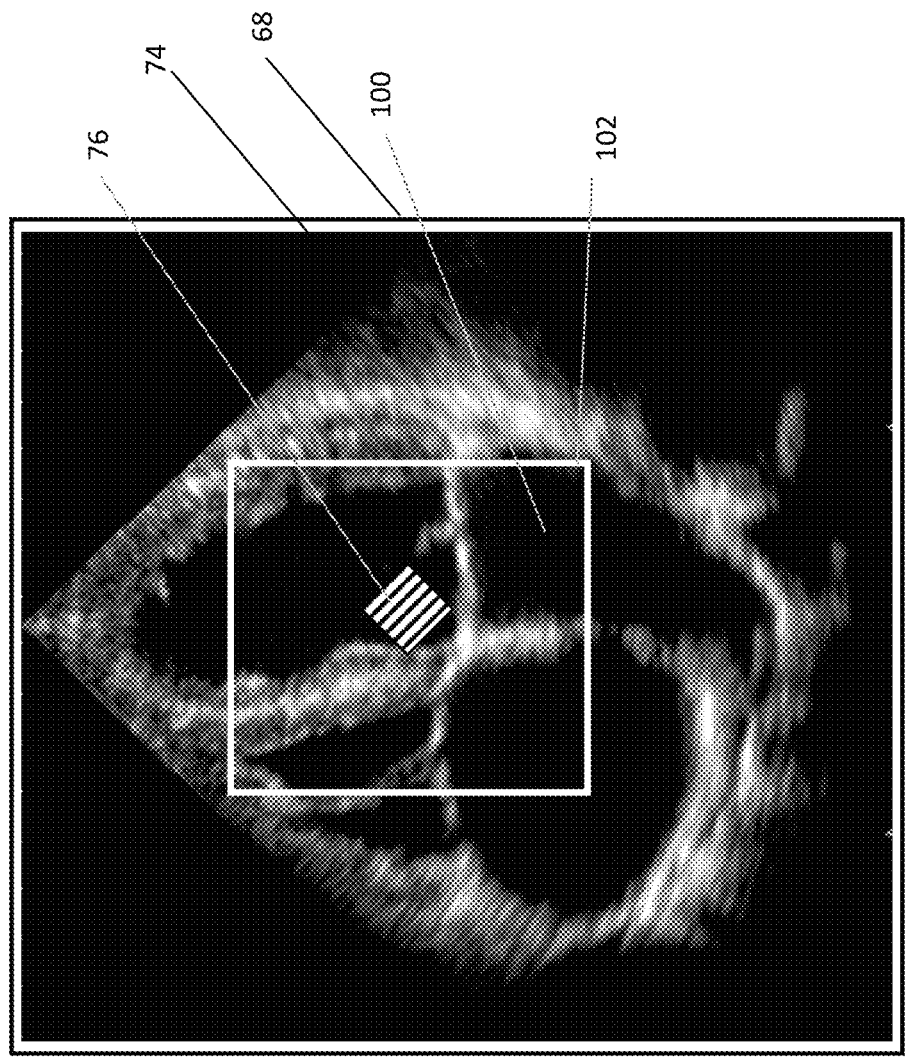
Figure 2C:
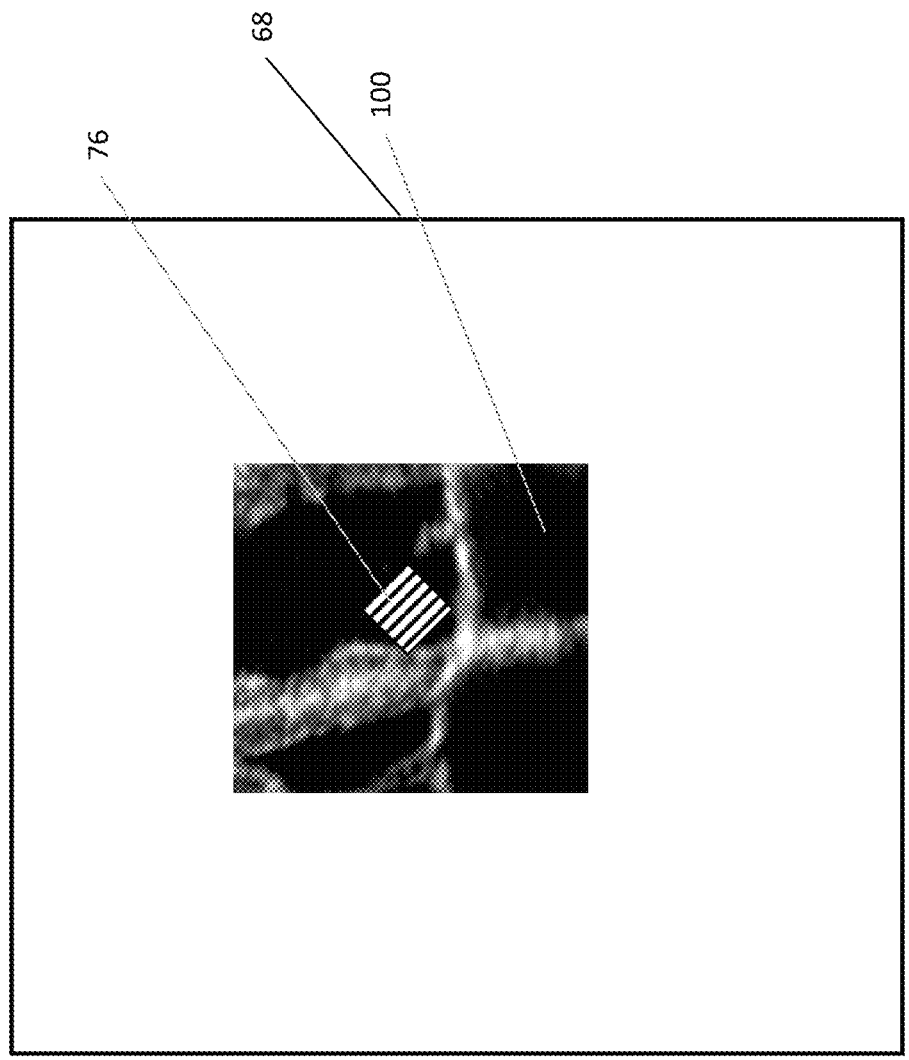

FIGS. 2A, 2B, and 2C are schematic representations of ultrasound images of heart 28, illustrating a process of selection of region of interest 100 for visualizing the distal end of ablation catheter 53, in accordance with an aspect of the invention. For the sake of simplicity, region of interest 100 is shown in FIGS. 2B and 2C as a 2D sub-set of ultrasound image 74 rendered to display screen 68, with icon 76 representing the distal end of catheter 53. However, as described hereinabove, the selection process in general involves rotating the full 3D ultrasound image and viewing selected 2D slices of the image in various orientations and positions.

FIG. 2A shows ultrasound image 74 of heart 28 rendered to display screen 68 before physician 72 selects the initial region of interest 100. FIG. 2B shows frame 102 superimposed by physician 72 on image 74 for defining the initial region of interest. FIG. 2C shows region of interest 100 with icon 76 after only that region of interest has been imaged by the ultrasound imaging sub-system and presented on display screen 68.

Figure 3A:
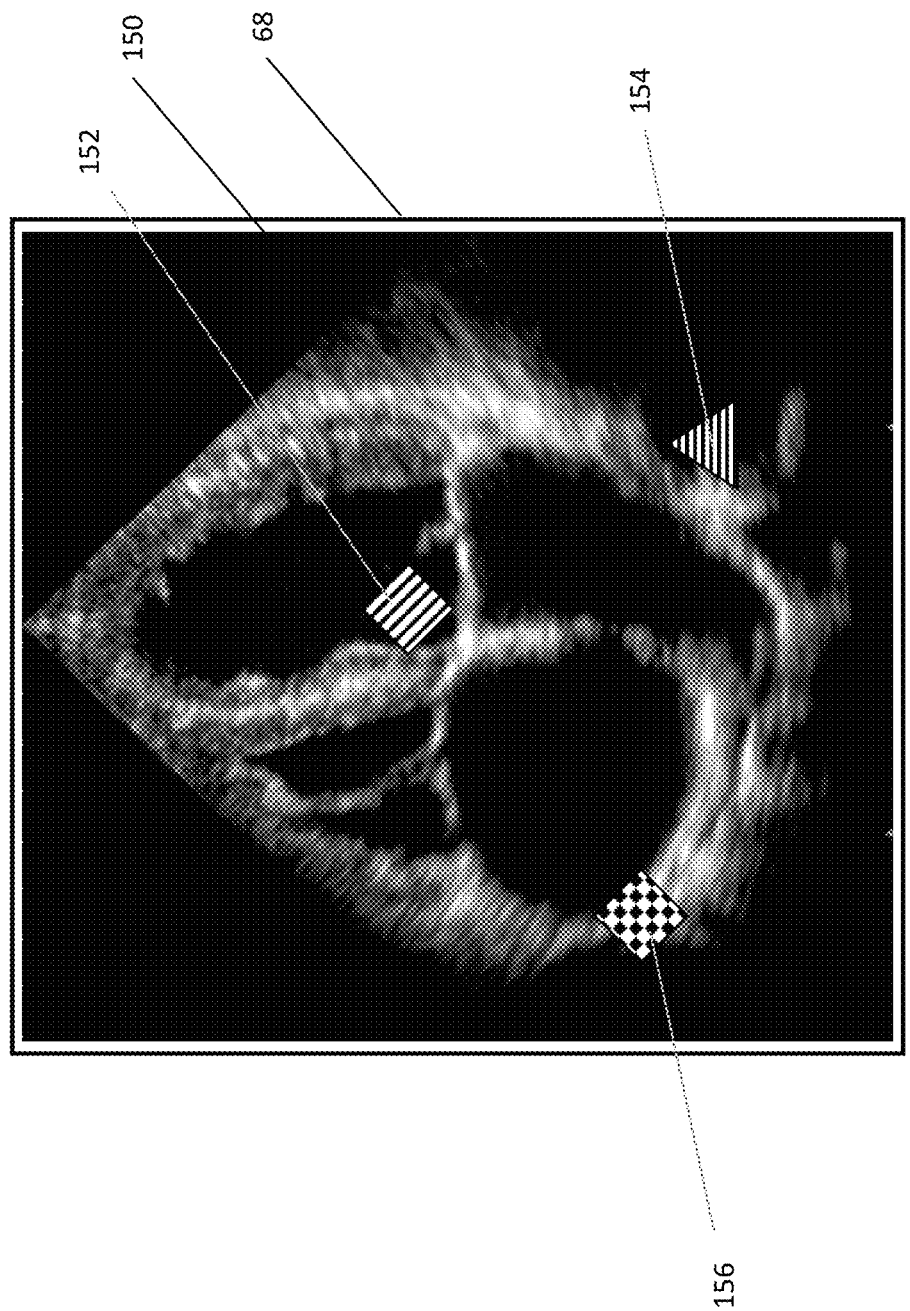
FIGS. 3A, 3B, and 3C are schematic representations of ultrasound images of a heart, illustrating a process of selection of regions of interest for visualizing multiple medical probes, in accordance with an aspect of the invention.
Figure 3B:
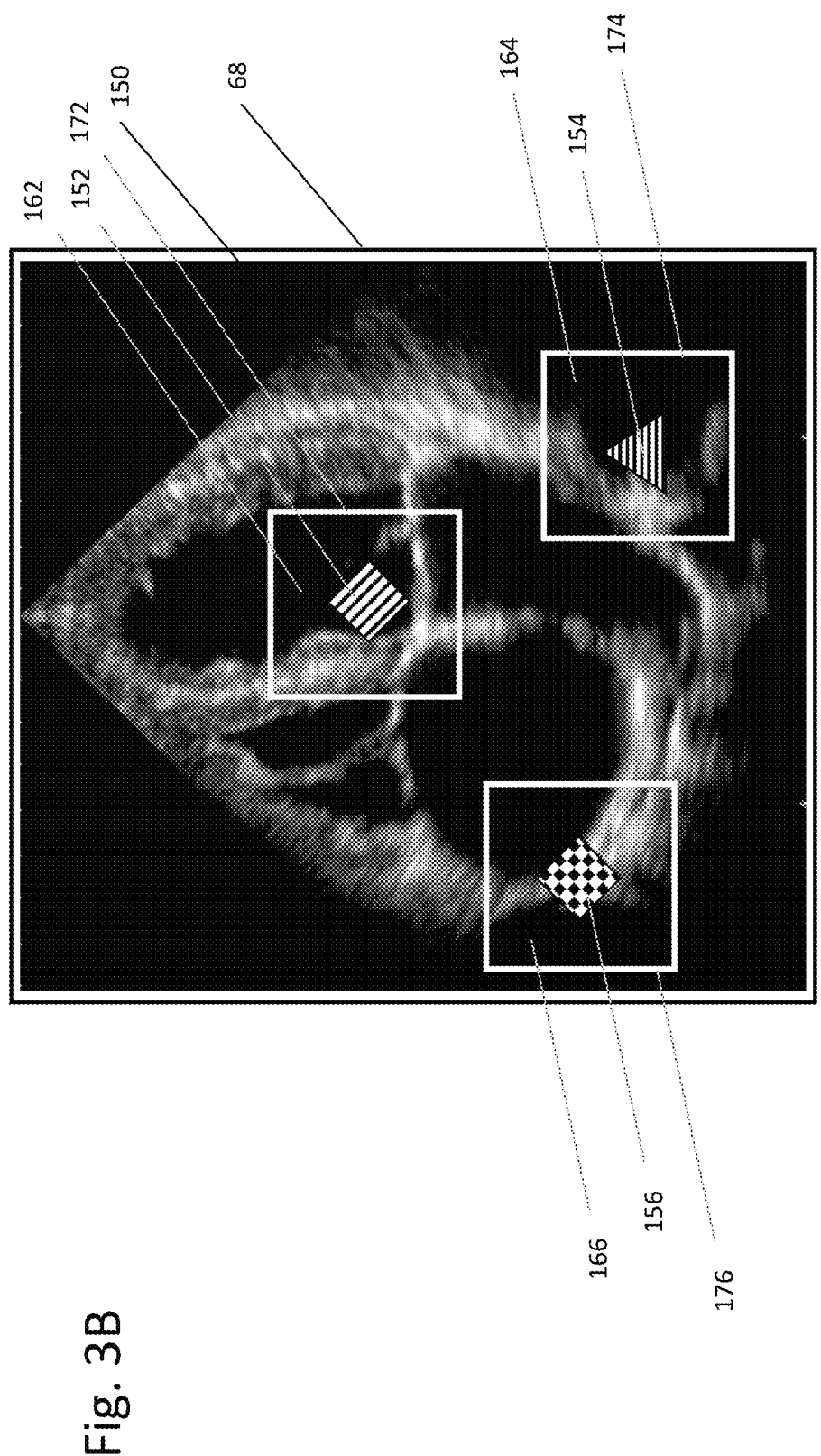
Figure 3C:
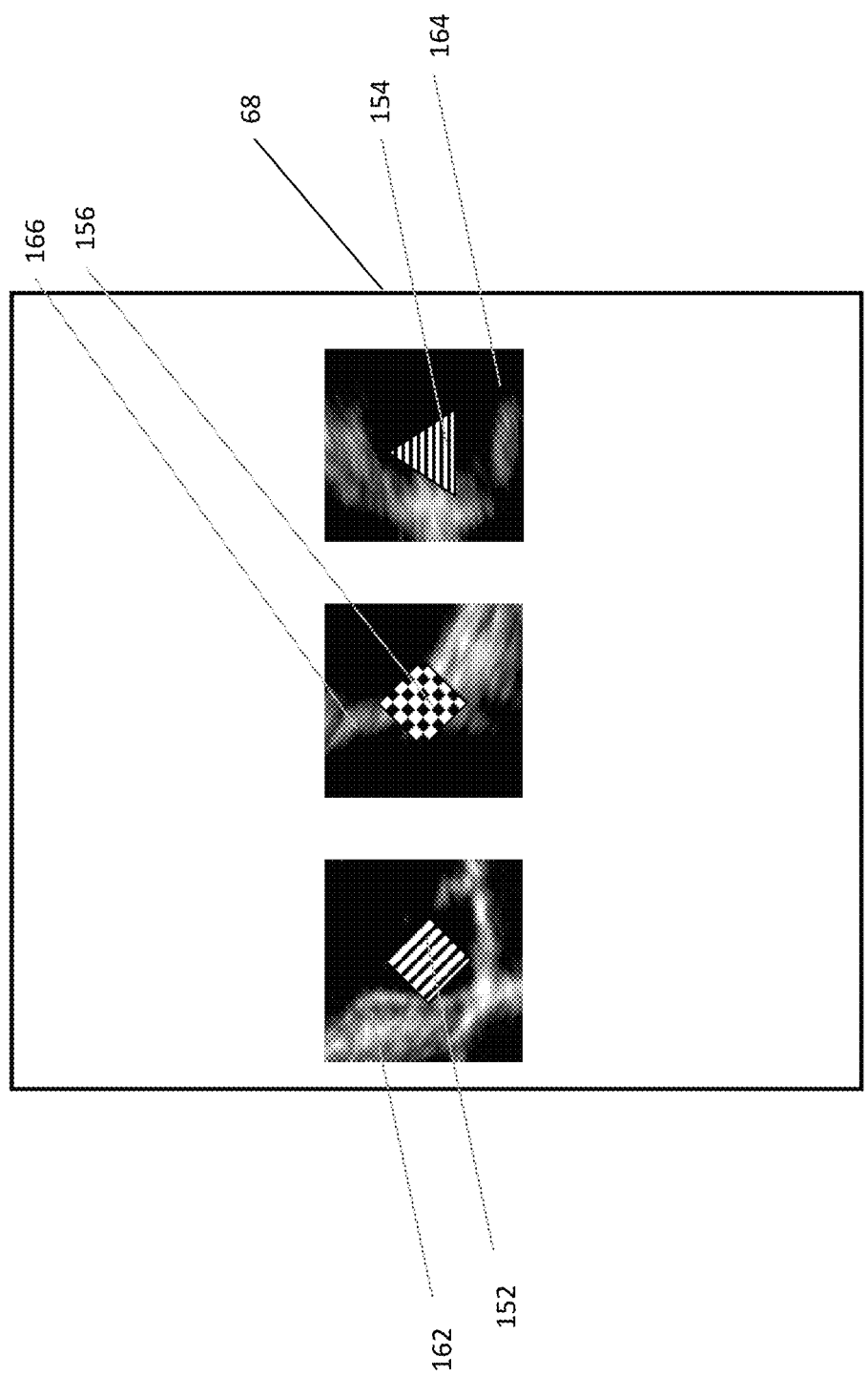

FIGS. 3A, 3B, and 3C are schematic representations of ultrasound images of heart 28, illustrating a process of selection of regions of interest for visualizing multiple medical probes within the heart, in accordance with another aspect of the invention.

FIG. 3A shows an ultrasound image 150 of heart 28 rendered to display screen 68. Icons 152, 154, and 156 are superimposed on image 150 to represent the positions of the respective medical probes within the image. Each icon 152, 154, and 156 has a unique shape and/or unique color in order to assist physician 72 in identifying each probe quickly and with a high level of confidence in ultrasound image 150. (Different colors are indicated in the figures by different hatch patterns.)

Similarly to the procedure for visualizing a single medical probe (described hereinabove), physician 72 selects from image 150 three regions of interest 162, 164, and 166, one for each of the three probes. The selection is marked in FIG. 3B by respective frames 172, 174, and 176.

After the selection, the ultrasound imaging sub-system images and displays only the selected regions of interest 162, 164, and 166, as shown in FIG. 3C. In FIG. 3C, regions of interest 162, 164, and 166 are arranged side-by-side on display screen 68. Alternatively, regions of interest 162, 164, and 166 may be displayed in a larger size one at a time in temporal succession.

Regions of interest 162, 164, and 166 may be selected either as 2D slices or 3D sub-volumes of the full 3D ultrasound image (or a combination of 2D slices and 3D sub-volumes). When 2D slices are selected, each slice may correspond to a different plane of the full 3D ultrasound image, thus enabling presenting each of the icons in a visually relevant environment. Selecting 2D slices or 3D sub-volumes enables, as previously described, higher frame rates and real-time observation of the probes.

For ablation catheter 53 with multiple electrodes 32 (FIG. 1), wherein the electrodes are pre-registered with position tracking device 54, each electrode may be shown as a separate icon in a selected region of interest.

Figure 4:
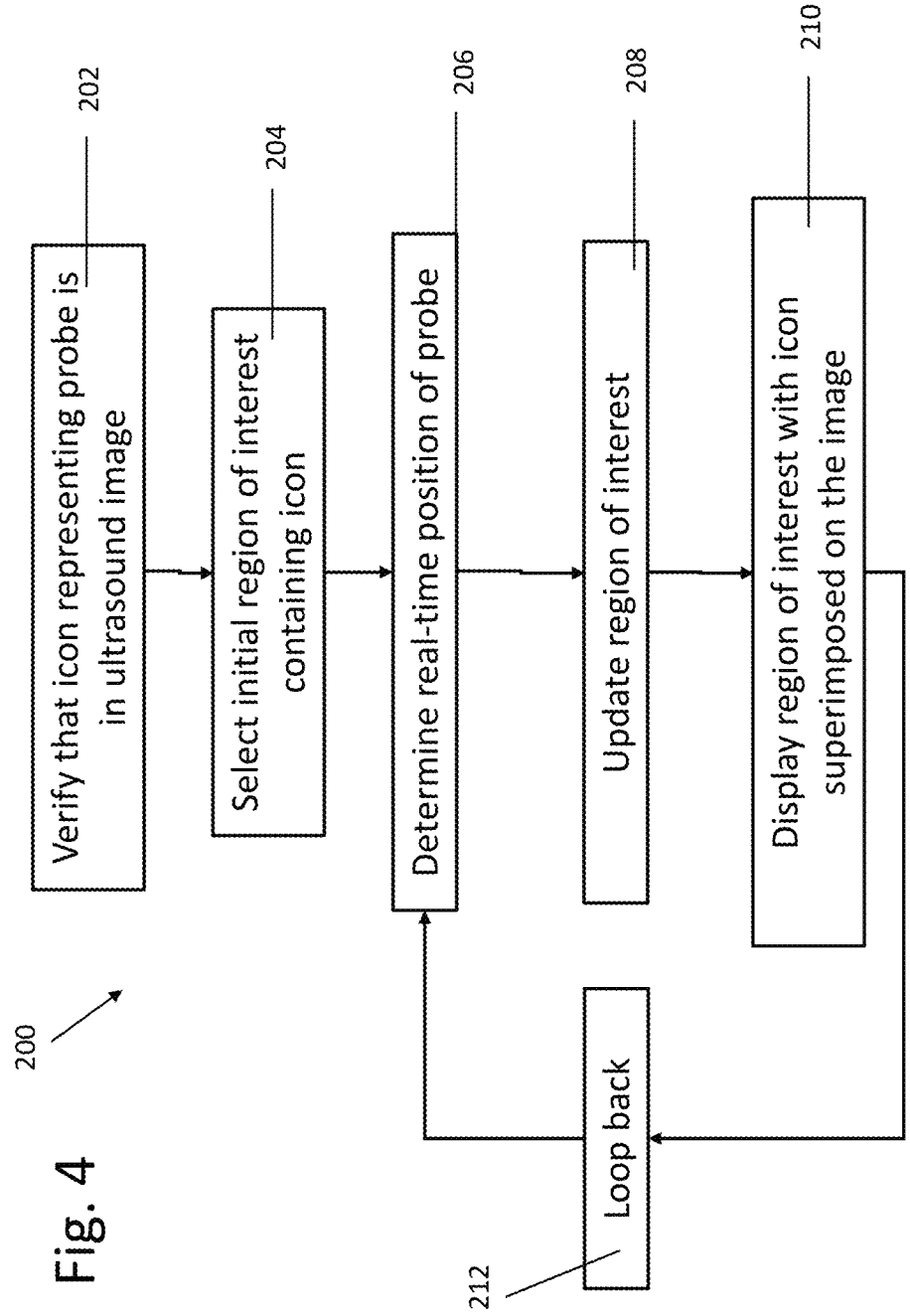
FIG. 4 is a flow chart that schematically illustrates a method for visualizing a medical probe in a 4D ultrasound image, in accordance with an aspect of the invention.

FIG. 4 is a flow chart 200 that schematically illustrates a method for visualizing the distal end of ablation catheter 53 in a 4D ultrasound image, in accordance with an aspect of the invention. With reference to FIG. 1 and to FIGS. 2A-2C, flow chart 200 illustrates the visualization of the distal end after physician 72 has already inserted ablation catheter 53 into heart 28.

In a verification step 202, physician 72 verifies that he sees icon 76, representing the position of the distal end of ablation catheter 53, in ultrasound image 74 rendered to display screen 68. (If physician 72 does not see icon 76 in ultrasound image 74, he/she will manipulate one or both of catheters 39 and 53 to bring the icon into the image.) In a selection step 204, physician 72 selects the initial region of interest 100 containing icon 76 as a 2D slice or a 3D sub-volume of image 74.

In a position determination step 206, processor 66 finds in real time the position of the distal end of ablation catheter 53 relative to ultrasound catheter 39, based on the signals output by respective tracking devices 42 and 54. In an update step 208, processor 66 updates the region of interest 100 based on the real time position of the distal end of ablation catheter 53. In this step, processor 66 may shift the location and/or orientation of the region of interest to accommodate changes in the position of the distal end of the ablation catheter, so that the region of interest continues to contain the distal end notwithstanding the changes in position. In a display step 210, processor 66 renders the updated region of interest 100 together with icon 76 to display screen 68. In a loop-back step 212, processor 66 returns back to position determination step 206 for updating the position of the distal end of ablation catheter 53 in order to account for further movements of the catheter during the procedure.

It will be appreciated that the features described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical imaging system, comprising:
a display screen;
an ultrasound imaging probe, configured to be inserted into a body of a living subject and to generate three-dimensional (3D) ultrasound images of tissue in the body;
a medical probe, which is configured to be inserted into the body and comprises a position tracking device and a transducer configured to contact the tissue, wherein the medical probe is one of a set of at least first and second medical probes, which comprise respective position tracking devices and are configured to be inserted into the body; and
a processor configured to receive the 3D ultrasound images, to receive from the position tracking devices position signals indicating a position of the at least first and second medical probes relative to the 3D ultrasound images, to select within the 3D ultrasound images, responsively to the indicated position, first and second regions of interest containing respective positions of the first and second medical probes, to simultaneously render both the first and second regions of interest to the display screen together with respective representations of the first and second medical probes, to detect a movement of the first medical probe, and to update the first region of interest based at least on the movement of the first medical probe without updating all of the 3D ultrasound images.

2. The medical imaging system according to claim 1, wherein the ultrasound imaging probe comprises a further position tracking device, and wherein the processor is configured to receive further signals from the further position tracking device indicating a location and orientation of the ultrasound imaging probe and to find the position of the medical probe relative to the 3D ultrasound images based on the position signals and the further signals.

3. The medical imaging system according to claim 1, wherein the region of interest comprises a two-dimensional (2D) slice of the 3D ultrasound images.

4. The medical imaging system according to claim 3, wherein the 2D slice is selected to contain the longitudinal axis of the medical probe.

5. The medical imaging system according to claim 3, wherein the 2D slice is selected to be perpendicular to a surface of the tissue that is contacted by the transducer.

6. The medical imaging system according to claim 1, wherein the region of interest comprises a 3D sub-volume of the 3D ultrasound images.

7. The medical imaging system according to claim 1, wherein the transducer comprises at least one electrode.

8. The medical imaging system according to claim 1, wherein the processor is configured to detect, responsively to the position signals, a change in the position of the probe relative to the 3D ultrasound images, and to update the selected region of interest responsively to the change.

9. The medical imaging system according to claim 8, wherein the processor is configured to receive an input from a user of the system indicating an initial region of interest containing the position of the medical probe, and to select and update the region of interest responsively to the input.

10. The medical imaging system according to claim 1, wherein the respective representations of the first and second medical probes comprise icons having different shapes.

11. The medical imaging system according to claim 1, wherein the respective representations of the first and second medical probes comprise icons having different colors.

12. A method for imaging, comprising:
receiving three-dimensional (3D) ultrasound images of tissue a body of a living subject from an ultrasound imaging probe within the body;
receiving position signals from a position tracking device in a medical probe that is inserted into the body, the medical probe further comprising a transducer spaced apart from the position tracking device and configured to contact the tissue;
computing, based on the position signals, a position of the medical probe relative to the 3D ultrasound images;
selecting within the 3D ultrasound images, responsively to the computed position, a region of interest that contains the position of the medical probe;
rendering the selected region of interest to a display screen together with a representation of the medical probe superimposed on the rendered region of interest;
detecting a change in position of the medical probe; and
updating, based at least on the change in position of the medical probe, the selected region of interest without updating all of the 3D ultrasound images.

13. The method according to claim 12, wherein the ultrasound imaging probe comprises a further position tracking device, and wherein computing the position comprises receiving further signals from the further position tracking device indicating a location and orientation of the ultrasound imaging probe, and finding the position of the medical probe relative to the 3D ultrasound images based on the position signals and the further signals.

14. The method according to claim 12, wherein the region of interest comprises a two-dimensional (2D) slice of the 3D images.

15. The method according to claim 14, wherein the 2D slice is selected to contain the longitudinal axis of the medical probe.

16. The method according to claim 14, wherein the 2D slice is selected to be perpendicular to a surface of the tissue that is contacted by the transducer.

17. The method according to claim 12, wherein the region of interest comprises a 3D sub-volume of the 3D images.

18. The method according to claim 12, wherein the transducer comprises at least one electrode.

19. The method according to claim 12, wherein computing the position comprises detecting, responsively to the position signals, a change in the position of the probe relative to the 3D ultrasound images, and wherein selecting the region of interest comprises updating the selected region of interest responsively to the change.

20. The method according to claim 19, wherein selecting the region of interest comprises receiving an input from a user indicating an initial region of interest containing the position of the medical probe, and selecting and updating the region of interest responsively to the input.

21. The method according to claim 12, wherein the medical probe is one of a set of at least first and second medical probes, which comprise respective position tracking devices and are inserted into the body, and
wherein selecting the region of interest comprises selecting within the 3D ultrasound images first and second regions of interest containing respective positions of the first and second medical probes, and rendering the selected region comprises rendering both the first and second regions of interest to the display screen together with respective representations of the first and second medical probes.

22. The method according to claim 21, wherein the respective representations of the first and second medical probes comprise icons having different shapes.

23. The method according to claim 21, wherein the respective representations of the first and second medical probes comprise icons having different colors.

* * * * *